United States Patent [19]

Curtis et al.

[11] Patent Number: 5,340,566
[45] Date of Patent: Aug. 23, 1994

[54] METHOD FOR PREVENTING THE PROGRESSION OF GINGIVITIS

[75] Inventors: John P. Curtis, Bloomsbury; Susan E. Greenfeder, Metuchen, both of N.J.; Bill Seiden, Syosset, N.Y.; Michael L. Lees, Basking Ridge, N.J.

[73] Assignee: Colgate-Palmolive Company, Piscataway, N.J.

[21] Appl. No.: 103,874

[22] Filed: Aug. 9, 1993

[51] Int. Cl.$^5$ .................. A61K 7/16; A61K 9/68
[52] U.S. Cl. ...................... 424/49; 424/48; 424/440
[58] Field of Search ................ 424/48, 49, 440

[56] References Cited

U.S. PATENT DOCUMENTS

| | | | |
|---|---|---|---|
| 4,029,760 | 6/1977 | De Roeek | 424/48 |
| 4,218,434 | 8/1980 | Rolla et al. | 424/49 |
| 4,775,525 | 10/1988 | Pera | 424/58 |
| 4,842,846 | 6/1989 | Nakano | 424/49 |
| 5,004,597 | 4/1991 | Majeti et al. | 424/52 |
| 5,028,414 | 7/1991 | Sampathkumar | 424/53 |
| 5,145,666 | 9/1992 | Lukacovic et al. | 424/52 |
| 5,185,153 | 2/1993 | Pollock | 424/440 |
| 5,188,817 | 2/1993 | Ozick | 424/49 |

OTHER PUBLICATIONS

Rekola Scand. J. Dent. Res. 89(5): 393-9 Oct. 1989.
Dodds et al Arch. Oral. Boil. 38(7): 623-6 Jul. 1993.
Mouton et al Acta Odontol Scand 33(1): 27-31 (1975).
Ainamo et al J. Clin. Periodontol 4(3): 151-160 Aug. 1977.
Ainamo et al J. Clin. Periodontol 6(6): 397-406 Dec. 1979.
Jensen J. Am. Dent. Assoc. 913(2): 262-266 Aug. 1986.
Jensen et al Br. Dent. J. 167(6): 204-8 Sep. 1989.
Park et al Am. J. Dent 3(5): 185-191 Oct. 1990 (chewing gum recommended adjunct to oral hygiene).
Steinberg, Louis et al, Reminieralizing Potential, Antiplaque and Antigingivitis Effects of Xylitol and Sorbitol Sweetened Chewing Gum, Clin. Preven. Den. vol. 14, No. 5, pp. 31-34 Sep./Oct. 1992.
M. Addy et al, Effects of Sugared and Sugar Free Chewing Gum on the accumulation of plaque and debris on teeth, J. Clin. Period. 1982:9:346-354.

*Primary Examiner*—Shep Rose
*Attorney, Agent, or Firm*—Paul Shapiro; Robert C. Sullivan

[57] ABSTRACT

A method is disclosed for treating and preventing gingivitis involving a patient desiring to prevent the progression of gingivitis the method comprising brushing the patient's teeth with a toothpaste at least two times a day and the patient chewing a chewing gum for at least 20 minutes at about two and about three hour intervals after having eaten each of at least two daily meals.

5 Claims, No Drawings

METHOD FOR PREVENTING THE PROGRESSION OF GINGIVITIS

BACKGROUND OF THE INVENTION

1. Field of the Invention

This invention relates to a novel method for the prevention of the onset and progression of gingivitis which method is practiced by a patient in accordance with a specific daily regimen of tooth brushing and chewing gum over an extended period of time.

2. The Prior Art

Periodontal disease is an inflammatory disorder of the gums variously referred to as gum disease, gingivitis and periodontitis. Gingivitis is defined as a reddening and swelling of the normally pink gums and may be accompanied by occasional bleeding. This inflammation is often progressive leading to ulceration of the gums and final destructive effect on the supporting tissues/fibers and bone which anchor the teeth. With the use of fluoride in drinking water, and daily use of toothpaste to help reduce tooth loss to decay, gum disease has become the largest cause of tooth loss in the adult population of the United States, accounting for approximately 70% of such losses.

The treatment of gingival tissues to maintain the health thereof conventionally comprises regular and periodic massaging of the gingival, flossing, tooth brushing and rinsing of the mouth on a regular basis; and deep scaling and curettage procedures performed by dentists. However such treatments are not fully effective to prevent the onset and progression of gingivitis. It is apparent then, that an improved means to prevent the onset and progression of gingivitis is needed in the oral hygiene field.

Chewing gum has been suggested by the prior art as a mechanical aid for cleaning teeth. For example, in the J. of Clinical Periodontology 1982:9:346–354 (1982) it is reported that clinical studies of the effects of chewing gum as a mechanical cleaning agent for teeth indicate that the although use by patients of chewing gum reduced plaque accumulation and salivary debris on teeth, the plaque removal occurred primarily from sites remote from gingival margins and interdental areas. It was concluded by this report that the observed effects of chewing gum on plaque would not be reflected in a reduction in gingival inflammation.

SUMMARY OF THE INVENTION

The present invention provides a procedure whereby the onset and progression of gingivitis can be unexpectedly substantially reduced by a regimen of daily toothbrushing combined with chewing gum at specific intervals following meals wherein the patient brushes his teeth at least two times daily preferably with a fluoride toothpaste followed by chewing a sugarless chewing gum for at least 20 minutes at about two and about three hour intervals after each of at least two meals which are eaten daily the regimen continuing over a period of at least 6 weeks time.

EXAMPLE OF INVENTION

The following example reports the results of a clinical study of the method of the present invention in the treatment of gingivitis.

To test the effectiveness of the method of the present invention 60 male/female adults were selected to participate in a plaque removal and gingivitis reduction effectiveness study.

Selection of patients for the study were based on the following factors:

a. Male or female aged 18 to 65 (inclusive).
b. Good general health.
c. Minimum of 20 natural uncrowned teeth, excluding third molars, with each of the 20 teeth having 18 scoring sites as required by the Rustogi Modification of the Modified Navy Index (J. Clin. Dent.: Suppl. 90–92).
d. Above average 24 hour plaque growth (average whole mouth plaque index of at least 0.60 based on the Rustogi modification of the Modified Navy Index.
e. Minimum gingivitis index of 1.4 based on the Löe-Silness Index (Acta Odonte Scand. 21:533, 1963).

Patients were excluded from the study if any of the following factors were found to be present on examination of the oral cavity.

a. Orthodontic appliances or partial dentures.
b. Soft or hard tumor of the oral cavity.
c. Five or more dental caries requiring immediate treatment.
d. Advanced periodontal disease characterized by the presence of purulent exudate, tooth mobility, and/or extensive alveolar bone loss.
e. Antibiotic therapy during the one month prior to the entry into the study.
f. Participation in another drug/dental clinical study.

Patients were removed from the study if they received routine dental treatment during the study or if they received emergency dental treatment that would influence plaque growth or if loss of teeth placed them below minimum tooth requirements.

Each patient was given a baseline gingivitis examination to determine the gingivitis index based on the Löe-Silvers Index, and a baseline plaque examination wherein plaque area was scored for the entire mouth using the Rustogi modification of the Modified Navy Index.

Each patient was given a commercial toothbrush and a tube of commercial fluoride toothpaste and instructed to brush their teeth with the assigned toothbrush in their usual manner. In addition, the patients were given packets of a commercial sugarless chewing gum and instructed to follow the afternoon and evening meal using a stick of the chewing gum at 2 and 3 hours after each meal and chewing each time for 20 minutes.

The patients were instructed to use only the assigned materials for a six week study period. No other oral hygiene was allowed for the six week study period. The patients were told to return in 3 weeks for a first examination and in six weeks for a final examination.

During the course of the study the patients were evaluated at three week and six week intervals using the same scoring procedures used for the plaque and gingivitis baseline examinations. On the day of each of the two evaluations, the patients were instructed not to chew gum or use any oral hygiene the morning prior to each evaluation.

The results of the clinical study are summarized in the Table below. The mean plaque and gingival index scores recorded in the Table show that the practice of the present invention is effective to reduce gingivitis to a level not ordinarily encountered in ordinary brushing of teeth and chewing of gum.

TABLE

| Mean Index Score For | Baseline | Week 3 | Week 6 |
|---|---|---|---|
| Plaque | 0.67 ± 0.03* | 0.65 ± 0.04 | 0.61 ± 0.04 |
| Gingival | 2.17 ± 0.18 | 1.98 ± 0.15 | 1.47 ± 0.28 |

*Standard deviation

The results recorded in the Table show a minimal decrease in the mean index score for plaque, but a substantial, (32%) decrease in the mean index gingival score.

By way of contrast, in a clinical study reported in Clinical Preventive Dentistry Vol. 14, No. 5 pgs 31-34 (September-October 1992) which study was designed to test the effects of xylitol and sorbitol sweetened chewing gums following six weeks of treatment, indicated only a minimal reduction (5-9%) of gingivitis in the patients tested who maintained their routine oral hygiene habits during the study.

In this reported clinical study, 28 subjects were randomly assigned to each of 3 phases (six weeks in duration) consisting of chewing xylitol gum, sorbitol gum and a non-chewing phase. The subjects were required to maintain their routine oral hygiene habits during the study. The subjects chewed five sticks of gum a day between and after meals for a recommended chewing time of ten minutes per stick. At the completion of each treatment phase, gingival indexes (Modified Silness-Loe, Acta Odontol Scand. 1963;21:533) were performed. Subjects met the following criteria: a) at least twenty sound permanent teeth not requiring extraction or immediate restoration; b) neuromuscular ability within normal limits; c) baseline gingival index of <1.5 (Modified Silness-Löe); e) not currently undergoing treatment for an acute medical condition (including, but not limited to, the use of antibiotics)in the weeks preceding and during the duration of the study; f) not chew any other gum, seek separate dental treatment or participate in another clinical study during duration of study.

The results of the 6 week study are reproduced below. (Table 2, page 33 of the reported study)

| Gingival Index (Modified Silness - Löe) | | |
|---|---|---|
|  | Mean | Standard Deviation |
| Initial Exam | 2.00 | 0.43 |
| Xylitol gum | 1.90 | 0.33 |
| Sorbitol gum | 1.82 | 0.42 |
| No gum | 2.00 | 0.39 |

The data recorded directly above indicates a 5% reduction in the mean gingival index obtained with patients chewing xylitol gum and a 9% reduction in the mean gingival index with subjects chewing sorbitol gum. The investigators in the reported study indicated that although the gingival indexes reflected a decrement in gingival inflammation with both xylitol and sorbitol gums, only the sorbitol gum values were considered to be statistically significant. The investigators further concluded that statistically there was no difference in the gingivitis scores between the sorbitol and xylitol gum use and that the statistical significance for sorbitol gum and not xylitol gum in the gingival index decrement noted was probably a reflection of the modest difference and relatively large standard deviations and their impact on the statistical analysis.

We claim:

1. A method of treating and preventing gingivitis involving a patient suffering from or wishing to prevent the progression of gingivitis, the method comprising the daily oral hygiene routine of brushing the patient's teeth with a toothpaste at least two times a day and the patient chewing a chewing gum for at least 20 minutes at about two and about three hour intervals after having eaten each of at least two daily meals, such routine being effective to reduce gingivitis to a level not attainable by either brushing of said toothpaste or chewing of said chewing gum, if either is employed alone.

2. The method of claim 1 wherein the toothpaste contains a fluoride compound.

3. The method of claim 1 wherein the chewing gum is sugarless.

4. The method of claim 1 wherein the method is practiced for an extended period of time.

5. The method of claim 4 wherein the period of time is at least 6 weeks.

* * * * *